United States Patent
Koizumi et al.

(10) Patent No.: US 8,106,237 B2
(45) Date of Patent: Jan. 31, 2012

(54) PROCESS FOR PRODUCING METHIONINE

(75) Inventors: Yoshiyuki Koizumi, Niihama (JP); Fumio Kubo, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 82 days.

(21) Appl. No.: 12/480,288

(22) Filed: Jun. 8, 2009

(65) Prior Publication Data
US 2009/0306426 A1   Dec. 10, 2009

(30) Foreign Application Priority Data
Jun. 9, 2008   (JP) .................... 2008-150898

(51) Int. Cl.
C07C 323/03   (2006.01)
(52) U.S. Cl. .................................................. 562/559
(58) Field of Classification Search .................. None
See application file for complete search history.

(56) References Cited

U.S. PATENT DOCUMENTS

| 4,303,621 A | 12/1981 | Lussling et al. |
| 5,770,769 A | 6/1998 | Geiger et al. |
| 5,945,563 A * | 8/1999 | Imi et al. ............... 562/559 |
| 2007/0055078 A1 | 3/2007 | Shiozaki et al. |

FOREIGN PATENT DOCUMENTS

| EP | 0 839 804 A2 | 5/1998 |
| EP | 1 564 208 A1 | 8/2005 |
| EP | 1 760 074 A1 | 3/2007 |
| EP | 1 840 119 A2 | 10/2007 |
| JP | 51-1415 A | 1/1976 |
| JP | 54-9174 B2 | 4/1979 |
| JP | 04-169570 A | 6/1992 |
| JP | 5-320124 A | 12/1993 |
| JP | 2007-63141 A | 3/2007 |
| JP | 2007-099778 A | 4/2007 |
| JP | EP 1760074 A1 * | 7/2007 |

OTHER PUBLICATIONS

European Search Report issued on Mar. 11, 2010 in corresponding European Patent Application No. 09 16 2185.
European Search Report issued on Mar. 11, 2010 in related European Patent Application No. 09 16 2182.
Search Report and Written Opinion dated Aug. 19, 2010, for Singapore Patent Application No. 20009038902.

* cited by examiner

*Primary Examiner* — Paul A Zucker
(74) *Attorney, Agent, or Firm* — Birch, Stewart, Kolasch & Birch, LLP

(57) ABSTRACT

The present invention provides a process for producing methionine, which comprises steps of:
hydrolyzing 5-[2-(methylthio)ethyl]imidazolidine-2,4-dione in the presence of a basic potassium compound in a non-stirred continuous first reaction tank, and
heat-treating the reaction solution after hydrolysis in a second reaction tank. According to the process of the present invention, a methionine crystal with a higher bulk density can be produced.

5 Claims, No Drawings

PROCESS FOR PRODUCING METHIONINE

BACKGROUND OF THE INVENTION

The present invention relates to a process for producing methionine by a hydrolysis reaction of 5-[(2-(methylthio) ethyl)]imidazolidine-2,4-dione [see the reaction scheme (1) shown below].

Reaction Scheme (1)

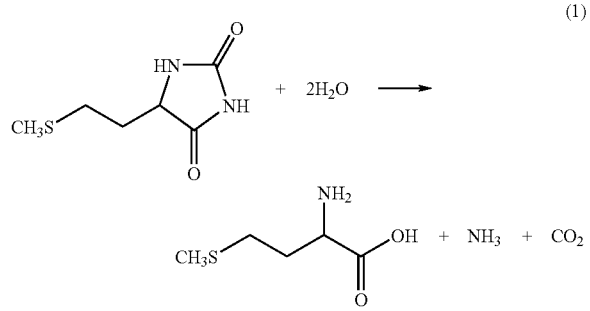

Methionine is useful as an additive for animal feed.

As an example of known processes for producing methionine, there is a process which comprises hydrolysis of 5-[(2-methylthio)ethyl]imidazolidine-2,4-dione under a basic condition using a basic potassium compound such as potassium carbonate or potassium hydrogen carbonate. According to this process, methionine can be separated and obtained as a crystal by introducing carbon dioxide into a reaction solution after hydrolysis to induce crystallization.

An example of the above-described methionine producing process which comprises carrying out hydrolysis in a stirred continuous reaction tank is disclosed (e.g., JP-A 2007-99778).

It is also known that a crystal of methionine is usually difficult to stabilize because it is a flake crystal, and therefore a flocculant is required for crystallization.

When hydrolysis is carried out in a stirred continuous reaction tank as described above, the resultant methionine crystal has a low bulk density, resulting in a high equipment cost.

SUMMARY OF THE INVENTION

An object of the present invention is to provide a process for producing a methionine crystal having a higher bulk density.

The present inventors have intensively studied and found that the amount of methionine dipeptide which is a by-product of hydrolysis in a reaction solution affects the bulk density of crystallized methionine, that is, when a larger amount of methionine dipeptide is contained in a reaction solution, crystallized methionine has a lower bulk density. Based on this finding, the present inventors have studied further. As a result, they have found that the amount of methionine dipeptide in a reaction solution can be reduced by carrying out hydrolysis in a non-stirred continuous reaction tank instead of a stirred continuous reaction tank, and the amount of methionine dipeptide can be further reduced by heat-treating the reaction solution to hydrolyze methionine dipeptide to methionine, so that the bulk density of crystallized methionine can be increased. Thus, the present invention has been completed.

The present invention provides:

[1] A process for producing methionine, which comprises steps of:
  hydrolyzing 5-[2-(methylthio)ethyl]imidazolidine-2,4-dione in the presence of a basic potassium compound in a non-stirred continuous first reaction tank, and
  heat-treating the reaction solution after hydrolysis in a second reaction tank;

[2] The process according to [1], wherein hydrolysis in the first reaction tank is carried out so that a conversion ratio of 5-[2-(methylthio)ethyl]imidazolidine-2,4-dione is 50% to 100%;

[3] The process according to [1], wherein the heating treatment in the second reaction tank is carried out at 150 to 200° C.;

[4] The process according to [1], wherein the heating treatment in the second reaction tank is carried out under a gauge pressure of 0.5 to 1.5 MPa;

[5] The process according to [1], wherein a total residence time in the first reaction tank and the second reaction tank is 10 to 120 minutes; and

[6] The process according to [1], which further comprises a step of introducing carbon dioxide into the reaction solution after heating treatment to induce crystallization.

In the hydrolysis of 5-[(2-(methylthio)ethyl)]imidazolidine-2,4-dione, methionine dipeptide as a by-product is produced by reaction of the product methionine with the starting material 5-[(2-(methylthio)ethyl)imidazolidine-2,4-dione. When the hydrolysis is carried out in a stirred continuous reaction tank, the starting material 5-[(2-(methylthio)ethyl)] imidazolidine-2,4-dione which is continuously added to the reaction tank and the product methione are accumulated in the reaction tank, and thus constant amounts of these compounds are always present in the reaction tank. Thereby, the by-product methionine dipeptide is always produced in a constant amount.

When the hydrolysis is carried out in a non-stirred continuous reaction tank (first reaction tank) instead of a stirred continuous reaction tank, the hydrolysis proceeds while the starting material 5-[(2-(methylthio)ethyl)]imidazolidine-2,4-dione which is continuously added moves through the tubular reaction tank, so that the amounts of the starting material 5-[(2-(methylthio)ethyl)]imidazolidine-2,4-dione and the product methionine vary at portions of the reaction tank. In other words, at an upper portion of the reaction tank, the amount of the starting material 5-[(2-(methylthio)ethyl)]imidazolidine-2,4-dione is larger and the amount of the product methionine is smaller. In contrast, at a lower portion of the reaction tank, the amount of the starting material 5-[(2-(methylthio)ethyl)]imidazolidine-2,4-dione is smaller and the amount of the product methionine is larger. Therefore, in the case of using a non-stirred continuous reaction tank, the amount of the by-product methionine dipeptide is reduced because one of the starting material 5-[(2-(methylthio)ethyl)] imidazolidine-2,4-dione and the product methionine is always smaller in amount than the other, unlike in the case of using a stirred continuous reaction tank wherein both compounds are always present in constant amounts.

After completion of the hydrolysis, a reaction solution containing a reduced amount of methionine dipeptide as described above is subjected to heating treatment, and thereby, methionine dipeptide is converted into methionine through hydrolysis and thus the final amount of methionine dipeptide produced as a by-product is further reduced.

DETAILED DESCRIPTION OF THE PREFERRED EMBODIMENTS

In the present invention, 5-[(2-(methylthio)ethyl)]imidazolidine-2,4-dione as a starting material is hydrolyzed in the presence of a basic potassium compound to obtain a reaction solution containing methionine in the form of a potassium salt [the reaction step (1)]. The starting material 5-[(2-(methylthio)ethyl)]imidazolidine-2,4-dione can be produced by, for example, reacting 2-hydroxy-4-methylthiobutanenitrile with ammonia and carbon dioxide or with ammonium carbonate [see the following reaction scheme (2) or (3)].

Reaction Scheme (2)

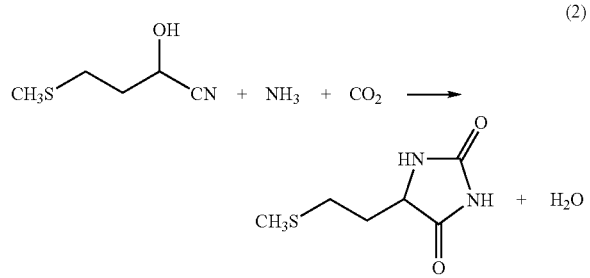

Reaction Scheme (3)

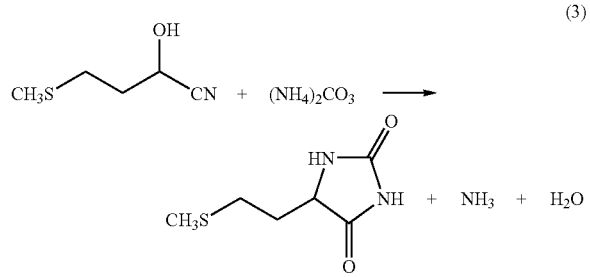

Examples of the basic potassium compound include potassium hydroxide, potassium carbonate and potassium hydrogen carbonate, and two or more of them can be used in combination, as needed. The used amount of the basic potassium compound is usually from 2 to 10 moles, preferably from 3 to 6 moles of potassium per 1 mol of 5-[(2-(methylthio)ethyl)]imidazolidine-2,4-dione. The used amount of water is usually from 2 to 20 times the weight of 5-[(2-(methylthio)ethyl)]imidazolidine-2,4-dione.

The hydrolysis reaction is preferably carried out under increased pressure at a gauge pressure of about 0.5 to 1 MPa while heating at about 150 to 200° C. The reaction time (residence time in the first reaction tank) is preferably 5 to 60 minutes, more preferably 10 to 30 minutes.

In the present invention, the hydrolysis is carried out in a non-stirred continuous reaction tank (first reaction tank).

The non-stirred continuous reaction tank is not particularly limited, and generally it may be in a tubular form. From the viewpoint of a reaction rate, it is preferable that the non-stirred continuous reaction tank approximates to a plug flow reactor.

Further, the first reaction tank is provided with a gas-vent line so as to distill off carbon dioxide and ammonia produced as by-products.

As described above, because the hydrolysis is carried out in a non-stirred continuous reaction tank, the amounts of the starting material 5-[(2-(methylthio)ethyl)]imidazolidine-2,4-dione and the product methionine vary at portions of the reaction tank and one of these compounds is smaller in amount than the other, so that the amount of methionine dipeptide produced as a by-product is reduced.

Next, the reaction solution containing a reduced amount of methionine dipeptide thus obtained is subjected to heating treatment in a second reaction tank. By the heating treatment, methionine dipeptide is converted into methionine through hydrolysis.

The heating treatment is carried out under increased pressure at a gauge pressure of preferably 0.5 to 1.5 MPa, more preferably 0.6 to 1 MPa, at preferably 150 to 200° C., more preferably 160 to 180° C. The heating treatment time (residence time in the second reaction tank) is preferably 5 to 60 minutes, more preferably 10 to 30 minutes.

It is preferable that the heating treatment is carried out until the proportion of methionine dipeptide to methionine reaches preferably 0.1 to 20% by weight, more preferably 1 to 10% by weight.

The type of the second reaction tank is not particularly limited. The type of the second reaction tank may be a batch-type or a continuous-type, and a stirred-type or an unstirred-type. From the viewpoint of equipment cost, it is preferable that the second reaction tank is a non-stirred continuous reaction tank.

The first reaction tank (unstirred continuous-type) can also serve as the second reaction tank. In this case, the tubular first reactor tank is equipped with a heating device between a middle portion and a lower portion of the reactor tank.

After the heating treatment, methionine is isolated from a reaction solution by the following procedure. Carbon dioxide is introduced into the reaction solution to induce crystallization, and the resultant slurry is separated into a precipitate and a mother liquor by filtration or decantation, thereby methionine is obtained as a precipitate [first crystallization step].

As a result of introduction of carbon dioxide, carbon dioxide is absorbed into the reaction solution, and thus a potassium salt of methionine is precipitated as free methionine.

The introduction of carbon dioxide is preferably carried out under increased pressure at a gauge pressure of usually 0.1 to 1 MPa, preferably 0.2 to 0.5 MPa.

The crystallization temperature is usually 0 to 50° C., preferably 10 to 30° C. The crystallization time can be determined on the basis of the time until the hydrolysis reaction solution is saturated with carbon dioxide to sufficiently precipitate methionine, and it is usually 30 minutes to 24 hours.

From the viewpoints of equipment cost and quality, the total residence time in the first and second reaction tank is preferably 10 to 120 minutes, more preferably 20 to 60 minutes.

Isolated methionine may be subjected to washing or pH adjustment as needed, and then dried to give a product. Drying is preferably carried out by heating at 50 to 120° C. under slightly reduced pressure. The drying time is usually 10 minutes to 24 hours.

A mother liquor after separation of methionine (hereinafter, referred to as a "first crystal mother liquor") still contains methionine in the amount corresponding to its solubility, and also contains potassium hydrogen carbonate, which can be recycled as the basic potassium compound. Therefore, it is preferable to recycle the first crystal mother liquor in the hydrolysis reaction. However, the first crystal mother liquor also contains impurities present in starting materials and impurities derived from a side reaction upon hydrolysis, for example, amino acids other than methionine, such as glycine and alanine, and coloring components. Therefore, recycling of the first crystal mother liquor allows these impurities to be introduced into hydrolysis reaction. Thus, it is necessary to recycle the first crystal mother liquor in not the entire amount but in such an amount that impurities are not accumulated. The recycling amount of the first crystal mother liquor is usually 50 to 90% by weight, preferably 70 to 90% by weight of the entire amount of the first crystal mother liquor.

For recycling of the first crystal mother liquor, it is preferable that the first crystal mother liquor is concentrated and the concentrate is used as a recycling solution. Through the concentration step, carbon dioxide can be distilled off from the first crystal mother liquor, and thus a recycling solution which has increased basicity and is advantageous to hydrolysis reaction can be obtained. Furthermore, a conversion reaction of potassium hydrogen carbonate in the first crystal mother liquor into potassium carbonate ($2KHCO_3 \rightarrow K_2CO_3+H_2O+CO_2$) is promoted by carrying out the concentration of the first crystal mother liquor at a high temperature of 100 to 140° C., and thus a recycling solution which has further increased basicity and is advantageous to hydrolysis reaction can be obtained. The concentration may be carried out under atmospheric pressure, reduced pressure or increased pressure. The concentration at high temperature as described above is carried out effectively under increased pressure. A concentration rate is usually from 1.2 to 4 times, preferably from 1.5 to 3.5 times. The "concentration rate" as used herein means the proportion of the weight of a solution before concentration to the weight of the solution after concentration (weight of solution before concentration/weight of solution after concentration).

The part of the first crystal mother liquor (concentrated first crystal mother liquor) which is not recycled is subjected to crystallization for the purpose of recovering methionine and potassium hydrogen carbonate as a second crystal. In the present invention, the second crystallization is accomplished by mixing the concentrated first crystal mother liquor with a lower alcohol and then introducing carbon dioxide into the mixed solution, and the resultant slurry is separated into a precipitate and a mother liquor by filtration or decantation to recover precipitated methionine and potassium hydrogen carbonate as a second crystal [second crystallization step]. It is also possible to subject the entire amount of the concentrated first crystal mother liquor to crystallization without recycling.

Examples of the lower alcohol include C1-C5 alkyl alcohols. Among them, preferred examples of the lower alcohol include alkyl alcohols miscible with water in a given ratio, such as methyl alcohol, ethyl alcohol, n-propyl alcohol, isopropyl alcohol and t-butyl alcohol, and particularly preferred is isopropyl alcohol. The used amount of the lower alcohol is usually 0.05 to 5 times, preferably 0.1 to 2 times the weight of the first crystal mother liquor subjected to crystallization. The first crystal mother liquor and the lower alcohol may be mixed before or simultaneously with introduction of carbon dioxide.

The first crystal mother liquor to be subjected to the second crystallization is concentrated before crystallization, similarly to the first crystal mother liquor to be recycled. Through the concentration step, a recovery rate of the second crystal can be increased. The concentration can be carried out under the same conditions as those for concentration of the first crystal mother liquor to be recycled. After the entire amount of the first crystal mother liquor is concentrated, the concentrate may be separated into two parts respectively for recycling and for second crystallization.

In the concentration step of the first crystal mother liquor, the basicity of the mother liquor increases and thereby the free methionine obtained by the first crystallization step returns to a potassium salt of methionine. Thus, also in the second crystallization step, carbon dioxide is introduced into the mixed solution of the concentrated first crystal mother liquor and the lower alcohol to convert a potassium salt of methionine into free methionine again.

Further, it is preferred that the first crystal mother liquor is heated after concentration, thereby hydrolyzing methionine dipeptide contained in the first crystal mother liquor to methionine. The heating treatment is carried out under increased pressure at a gauge pressure of about 0.5 to 2 MPa and preferably at 140 to 180° C. The heating treatment time is usually 10 minutes to 24 hours.

The introduction of carbon dioxide is carried out under increased pressure at a gauge pressure of usually 0.1 to 1 MPa, preferably 0.2 to 0.5 MPa, similarly to the first crystallization step.

The crystallization temperature is usually 0 to 50° C., preferably 5 to 20° C. The crystallization time may be determined on the basis of the time until the mixed solution is saturated with carbon dioxide to sufficiently precipitate methionine and potassium hydrogen carbonate, and is usually 10 minutes to 24 hours.

It is preferable that the second crystal (mixture of methionine and potassium hydrogen carbonate) thus recovered is recycled in the hydrolysis reaction. In this case, it is preferable in view of operability that the recovered second crystal is dissolved in the first crystal mother liquor for recycling and then subjected to recycling.

A mother liquor after separation of the second crystal (hereinafter, referred to as a "second crystal mother liquor") still contains methionine and potassium hydrogen carbonate. Thus, in the present invention, further methionine and potassium hydrogen carbonate are recovered as a third crystal from the second crystal mother liquor by the following procedure. Carbon dioxide is introduced into a concentrate of the second crystal mother liquor to induce crystallization, and the resultant slurry is separated into a precipitate and a mother liquor by filtration or decantation to recover methionine and potassium hydrogen carbonate as a third crystal [third crystallization step].

Through the concentration of the second crystal mother liquor, a recovery rate of the third crystal can be increased. The concentration can be carried out under the same conditions as those for concentration of the first crystal mother liquor to be recycled.

Further, it is preferred that the second crystal mother liquor is heated after concentration, thereby hydrolyzing methionine dipeptide contained in the second crystal mother liquor to methionine. The heating treatment is carried out under increased pressure at a gauge pressure of about 0.5 to 2 MPa and preferably at 150 to 200° C. The heating treatment time is preferably 0.3 to 10 hours.

It is preferable that the heating treatment is carried out until the proportion of methionine dipeptide to methionine reaches preferably 5 to 50% by weight, more preferably 5 to 30% by weight.

Also in the concentration step of the second crystal mother liquor, the basicity of the mother liquor increases and thereby the free methionine obtained by the second crystallization step returns to a potassium salt of methionine. Thus, also in the third crystallization step, carbon dioxide is introduced into the concentrated and heated second crystal mother liquor to convert a potassium salt of methionine into free methionine again.

The introduction of carbon dioxide is carried out under increased pressure at a gauge pressure of usually 0.1 to 1 MPa, preferably 0.2 to 0.5 MPa, similarly to the first crystallization step and the second crystallization step.

The crystallization temperature is usually 0 to 50° C., preferably 5 to 30° C. The crystallization time may be determined on the basis of the time until the concentrated and heated second crystal mother liquor is saturated with carbon dioxide to sufficiently precipitate methionine and potassium hydrogen carbonate, and is usually 10 minutes to 24 hours.

The third crystallization step is preferably carried out in the presence of polyvinyl alcohol, for example, as shown in JP-A 4-169570. The presence of polyvinyl alcohol upon crystallization allows the third crystal to be precipitated in a good deliquoring form and thereby, upon the subsequent solid-liquid separation, a mother liquor hardly remains in the third crystal. As a result, the content of impurities in the recovered third crystal can be reduced. The used amount of polyvinyl alcohol is usually 100 to 5,000 ppm by weight, preferably 200 to 3,000 ppm by weight in the concentrate of the second crystal mother liquor.

The first and second crystallization steps can also be carried out in the presence of polyvinyl alcohol. It is particularly preferable that the first crystallization step is carried out in the presence of polyvinyl alcohol because methionine having a good product powder property can be obtained.

The third crystal (mixture of methionine and potassium hydrogen carbonate) thus recovered is preferably recycled in the hydrolysis reaction, similarly to the second crystal.

All of the above-described crystallization steps may be carried out continuously or batch-wise. Alternatively, some of the above-described crystallization steps may be carried out continuously and some of them may be carried out batch-wise.

EXAMPLES

Hereinafter, the present invention will be explained by means of Examples. The present invention is not limited thereto. In Examples, the terms "%" and "part(s)" means concentration or a used amount based on weight, unless otherwise specified.

Example 1

Into a non-stirred continuous first reaction tank, 5.4 parts per hour of a mixture of a solution containing 5-[2-(methylthio)ethyl]imidazolidine-2,4-dione and a potassium hydroxide aqueous solution was continuously charged. While carbon dioxide and ammonia produced as by-products were continuously distilled off together with water, the reaction solution was continuously charged into a second non-stirred continuous reaction tank which was different from the first reaction tank. At this point, the temperature of the reaction tanks was 177° C. and the gauge pressure was 0.88 MPa. The residence time in the first reactor was 30 minutes, and the residence time in the second reaction tank was 6 minutes, totaling 36 minutes. After reaction, the hydrolyzed solution thus obtained contained 10.4% of potassium, 13.1% of methionine, and 1.29% of methionine dipeptide, and the proportion of methionine dipeptide to methionine was 9.9%.

Into a reactor, 1 part of the hydrolyzed solution was charged, and then, polyvinyl alcohol as a flocculent was charged in an amount of 2,300 ppm by weight of the methionine content of the hydrolyzed solution. Thereto carbon dioxide was introduced under stirring, followed by batch-wise neutralization crystallization. Then, while 2 parts per hour of the hydrolyzed solution and polyvinyl alcohol in an amount of 1,200 ppm by weight of the supplied methionine content were supplied, thereto carbon dioxide was introduced at a gauge pressure of 0.35 MPa under stirring, followed by semi-continuous neutralization crystallization at 15° C. for 1 hour. The methionine slurry thus obtained was separated using a centrifugal machine, washed with water, and then dried to give methionine powder. The bulk density of the methionine powder was 0.703 g/cc as measured according to a procedure described below.

Comparative Example 1

Into a first reaction tank, 5.9 parts per hour of a mixture of a solution containing 5-[2-(methylthio)ethyl]imidazolidine-2,4-dione and a potassium hydroxide aqueous solution was continuously charged, and carbon dioxide and ammonia produced as by-products were continuously distilled off together with water. At this point, the temperature of the reaction tanks was 177° C. and the gauge pressure was 0.88 MPa. The residence time in the first reactor was 36 minutes. After reaction, the reaction solution thus obtained contained 10.4% of potassium, 13.9% of methionine, and 1.64% of methionine dipeptide, and the proportion of methionine dipeptide to methionine was 11.8%. A crystallization and drying steps of methionine were carried out in the same manner as Example 1 to give methionine powder. The bulk density of the methionine powder was 0.665 g/cc as measured according to a procedure described below.

Measurement of Bulk Density

Dried powder was carefully put in a 50 cc volumetric cylinder. The weight W [g] and bulk V [cc] of the powder were measured without tapping. A bulk density was calculated according to the following equation.

$$\text{Bulk Density [g/cc]} = W/V$$

According to the present invention, because the hydrolysis is carried out in a non-stirred continuous reaction tank, the amounts of the starting material 5-[(2-(methylthio)ethyl)]imidazolidine-2,4-dione and the product methionine vary at portions of the reaction tank and one of these compounds is smaller in amount than the other. As a result, the amount of methionine dipeptide produced as a by-product is reduced. After completion of the hydrolysis, the reaction solution containing a reduced amount of methionine dipeptide thus obtained is subjected to heating treatment and thereby, methionine dipeptide is converted into methionine through hydrolysis and thus the final amount of methionine dipeptide produced as a by-product is further reduced.

What is claimed is:

1. A process for producing methionine, which comprises steps of:
   hydrolyzing 5-[2-(methylthio)ethyl]imidazolidine-2,4-dione in the presence of a basic potassium compound selected from the group consisting of potassium hydroxide, potassium carbonate, potassium hydrogen carbonate, and two or more of them in a non-stirred continuous first reaction tank, and
   heat-treating the reaction solution after hydrolysis in a second reaction tank at 150 to 200° C. until the proportion of methionine dipeptide to methionine reaches 0.1 to 10% by weight.

2. The process according to claim 1, wherein hydrolysis in the first reaction tank is carried out so that a conversion ratio of 5-[2-(methylthio)ethyl]imidazolidine-2,4-dione is 50% to 100%.

3. The process according to claim 1, wherein the heating treatment in the second reaction tank is carried out under a gauge pressure of 0.5 to 1.5 MPa.

4. The process according to claim 1, wherein a total residence time in the first reaction tank and the second reaction tank is 10 to 120 minutes.

5. The process according to claim 1, which further comprises a step of introducing carbon dioxide into the reaction solution after heating treatment to induce crystallization.

* * * * *